(12) United States Patent
Ondersma et al.

(10) Patent No.: US 9,931,231 B2
(45) Date of Patent: Apr. 3, 2018

(54) SUPPORT STRUCTURES FOR PROSTHESES WITH BRANCHING PORTIONS

(71) Applicant: COOK MEDICAL TECHNOLOGIES LLC, Bloomington, IN (US)

(72) Inventors: Joel Ondersma, Bloomington, IN (US); Edwin E. Macatangay, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 52 days.

(21) Appl. No.: 14/977,014

(22) Filed: Dec. 21, 2015

(65) Prior Publication Data

US 2016/0184115 A1 Jun. 30, 2016

Related U.S. Application Data

(60) Provisional application No. 62/097,474, filed on Dec. 29, 2014.

(51) Int. Cl.
| | | |
|---|---|---|
| *A61F 2/07* | (2013.01) | |
| *A61F 2/856* | (2013.01) | |
| *A61F 2/86* | (2013.01) | |
| *A61F 2/06* | (2013.01) | |

(52) U.S. Cl.
CPC .............. *A61F 2/856* (2013.01); *A61F 2/07* (2013.01); *A61F 2/86* (2013.01); *A61F 2002/061* (2013.01); *A61F 2250/0039* (2013.01)

(58) Field of Classification Search
CPC .... A61F 2/856; A61F 2/86; A61F 2/07; A61F 2002/061; A61F 2002/072–2002/075; A61F 2/88; A61F 2250/0039; A61F 2250/0018; A61F 2250/0029; A61F 2250/006

See application file for complete search history.

(56) References Cited

U.S. PATENT DOCUMENTS

| | | |
|---|---|---|
| 6,325,826 B1 | 12/2001 | Vardi et al. |
| 6,676,696 B1 | 1/2004 | Marotta et al. |
| 7,105,020 B2 | 9/2006 | Greenberg et al. |

(Continued)

FOREIGN PATENT DOCUMENTS

| | | | |
|---|---|---|---|
| CN | 103720529 | 4/2014 | |
| WO | WO2004026180 A2 * | 4/2004 | ............... A61F 2/82 |

OTHER PUBLICATIONS

Extended European Search Report for EP15275274 dated Jun. 1, 2016, 7 pgs.
Office Action dated Aug. 8, 2017 for EP15275274.7, 3 pgs.

*Primary Examiner* — Paul Prebilic
(74) *Attorney, Agent, or Firm* — Brinks Gilson & Lione

(57) ABSTRACT

The present embodiments provide an endoluminal prosthesis, comprising a prosthetic trunk and a prosthetic branch, each comprising proximal and distal ends and a lumen extending therebetween. The proximal end of the prosthetic branch is secured around an aperture formed in a side surface of the prosthetic trunk. A support structure is coupled to the prosthetic branch. In certain embodiments, a proximal end of the support structure comprises a first width, and a distal end of the support structure comprises a second width, wherein the first width is less than the second width.

17 Claims, 2 Drawing Sheets

(56) References Cited

U.S. PATENT DOCUMENTS

| | | |
|---|---|---|
| 7,407,509 B2 | 8/2008 | Greenberg et al. |
| 7,435,253 B1 | 10/2008 | Hartley et al. |
| 7,731,743 B2 | 6/2010 | Khosravi et al. |
| 7,842,082 B2 | 11/2010 | Yadin |
| 8,007,528 B2 | 8/2011 | Yadin et al. |
| 8,043,366 B2 | 10/2011 | Brown et al. |
| 8,529,618 B2 | 9/2013 | Davis et al. |
| 2006/0095118 A1 | 5/2006 | Hartley |
| 2006/0136046 A1 | 6/2006 | Hartley et al. |
| 2007/0225796 A1* | 9/2007 | Yadin ..................... A61F 2/856 623/1.16 |
| 2008/0177373 A1 | 7/2008 | Huang et al. |
| 2009/0125095 A1 | 5/2009 | Bui et al. |
| 2010/0100168 A1 | 4/2010 | Chuter et al. |
| 2010/0268319 A1* | 10/2010 | Bruszewski ............... A61F 2/07 623/1.13 |
| 2011/0270380 A1 | 11/2011 | Bruszewski |
| 2012/0290068 A1 | 11/2012 | Roeder et al. |

\* cited by examiner

SUPPORT STRUCTURES FOR PROSTHESES WITH BRANCHING PORTIONS

PRIORITY CLAIM

This invention claims the benefit of priority of U.S. Provisional Application Ser. No. 62/097,474, entitled "Support Structures for Prostheses with Branching Portions," filed Dec. 29, 2014, the disclosure of which is hereby incorporated by reference in its entirety.

BACKGROUND

The present embodiments relate generally to medical devices, and more particularly, to prostheses having branching portions.

The functional vessels of human and animal bodies, such as blood vessels and ducts, occasionally weaken or even rupture. For example, the aortic wall can weaken, resulting in an aneurysm. Upon further exposure to hemodynamic forces, such an aneurysm can rupture. One study found that in Western European and Australian men who are between 60 and 75 years of age, aortic aneurysms greater than 29 mm in diameter are found in 6.9% of the population, and those greater than 40 mm are present in 1.8% of the population.

One surgical intervention for weakened, aneurysmal, or ruptured vessels involves the use of an endoluminal prosthesis such as a stent-graft. Such a prosthesis may provide some or all of the functionality of the original, healthy vessel and/or preserve any remaining vascular integrity by replacing a length of the existing vessel wall that spans the site of vessel failure. It is preferable for the prosthesis to seal off the failed portion of the vessel. For weakened or aneurysmal vessels, even a small leak in the prosthesis may lead to the pressurization of or flow in the treated vessel which may aggravate the condition that the prosthesis was intended to treat.

In many cases, such a damaged or defective portion of the vasculature may include a branch vessel. For example, the celiac, superior mesenteric, left common carotid, and renal arteries are branch vessels of the aorta, and the internal iliac artery is a branch vessel of the common iliac artery. If the branch vessel is blocked by the prosthesis, the original blood circulation is impeded, and the patient can suffer. If, for example, the celiac artery is blocked by the prosthesis, the patient can experience abdominal pain, weight loss, nausea, bloating, and loose stools associated with mesenteric ischemia. The blockage of any branch vessel is usually associated with unpleasant or even life-threatening symptoms. Hence, it has been proposed to provide a prosthesis having a side branch which, when deployed, is positioned over the opening to a branch vessel. For example, the iliac branch of a bifurcated aortic prosthesis can be designed to extend into and/or provide flow to the corresponding internal iliac artery. Such a prosthesis is commonly referred to as an iliac branch device (IBD).

Various devices have incorporated a circumferential stent around the location of the coupling of the branch portion and trunk portion of a prosthesis. For example, a stent may encircle the trunk portion and then extend external to the branch portion, which is a general approach to keeping both the trunk and branch portions open at the same time.

SUMMARY

The present embodiments provide an endoluminal prosthesis comprising a prosthetic trunk and a prosthetic branch, each comprising proximal and distal ends and a lumen extending therebetween. The proximal end of the prosthetic branch is secured around an aperture formed in a side surface of the prosthetic trunk. A support structure is coupled to the prosthetic branch. In certain embodiments, the proximal end of the support structure comprises a first width, and the distal end of the support structure comprises a second width, wherein the first width is less than the second width.

The support structure may extend less than 360 degrees circumferentially in a deployed state. The support structure may comprise a deployed state having a concave shape relative to the prosthetic trunk.

In one example, the support structure comprises boundaries forming a pattern that corresponds to a shape of the aperture in the prosthetic trunk. In further examples, the aperture formed in the prosthetic trunk comprises an outer perimeter, and in an expanded state the support structure is positioned above the aperture in a manner radially outside of the aperture and within axial boundaries formed by the outer perimeter of the aperture.

A coil may be coupled to the prosthetic branch and disposed distally of the support structure. Alternatively, a Z-stent may be coupled to the prosthetic branch and disposed distally of the support structure.

The support structure coupled to the prosthetic branch may lack an attachment to the prosthetic trunk.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure.

Figure 1:
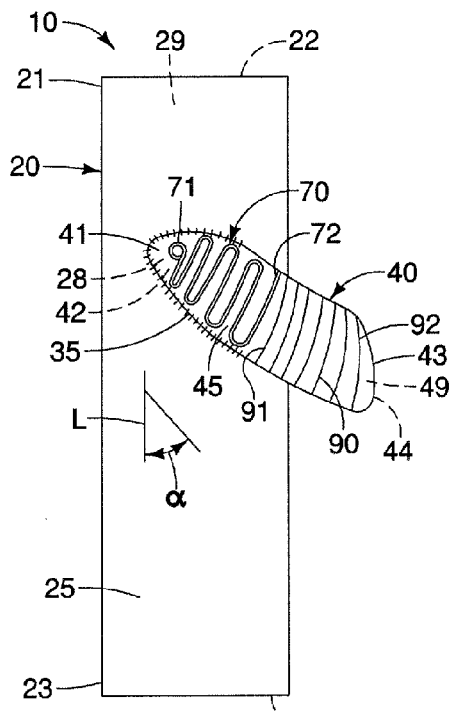
FIG. 1 is a front view of a first embodiment of a prosthesis having a prosthetic branch comprising a support structure.
Figure 2:
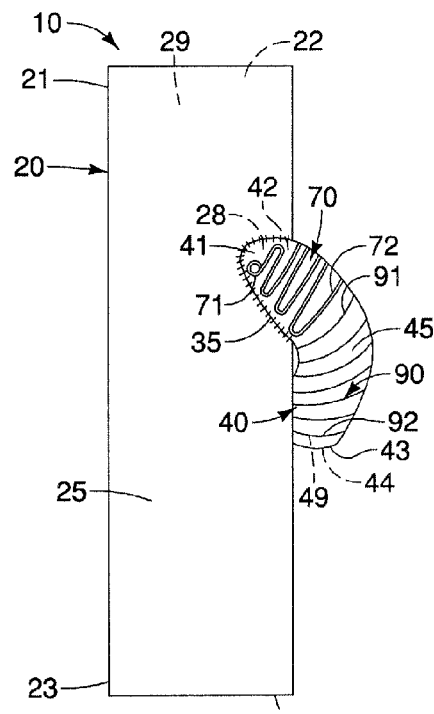
FIG. 2 is a side view of the prosthesis of FIG. 1.

FIGS. 1-2 depict one embodiment of a prosthesis 10 having a prosthetic trunk 20 and a prosthetic branch 40. The prosthetic trunk 20 has a first end 21 with a first end opening 22 and a second end 23 with a second end opening 24. The prosthetic trunk 20 can include a substantially tubular graft body 25 having inner and outer surfaces. The graft body 25 may form a generally cylindrical configuration. The inner surface of the graft body 25 can define a trunk lumen 29 extending longitudinally between the first end 21 and the second end 23 of the prosthetic trunk 20. The trunk lumen 29 may be suitable for passing fluid therethrough. The prosthetic trunk 20 may further include at least one support structure 60, as explained in further detail below.

The prosthetic branch 40 has a first end 41 with a first end opening 42 and a second end 43 with a second end opening 44. The prosthetic branch 40 can include a substantially tubular graft body 45 having inner and outer surfaces. The graft body 45 may form a generally cylindrical configuration. The inner surface of the graft body 45 can define a branch lumen 49 extending longitudinally between the first end 41 and the second end 43 of the prosthetic branch 40. The branch lumen 49 may be suitable for passing fluid therethrough. The prosthetic branch 40 further can include at least one support structure 70, as explained in further detail below.

The first end 41 of the prosthetic branch 40 may be attached to the prosthetic trunk 20 so that the prosthetic branch 40 may extend from the graft body 25 of the prosthetic trunk 20. The prosthetic branch 40 may extend from the prosthetic trunk 20 at various angles with respect to the graft body 25 of the prosthetic trunk.

Figure 3:
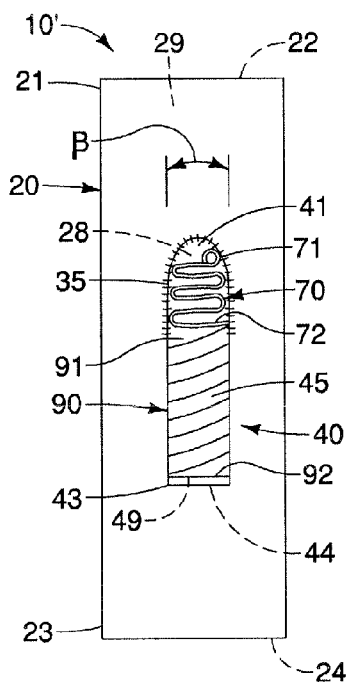
FIG. 3 is a front view of an alternative embodiment of a prosthesis having a prosthetic branch comprising a support structure.
Figure 4:
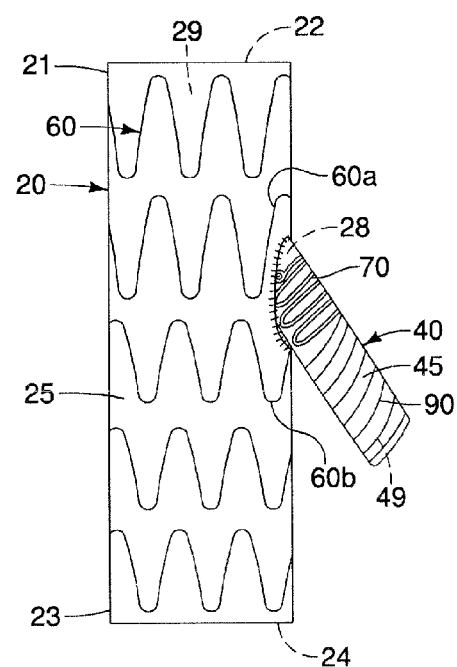
FIG. 4 is a side view of the prosthesis of FIG. 3.

In the embodiment of FIGS. 1-2, the prosthetic branch 40 has a "take-off angle" α of approximately 45 degrees relative to a longitudinal axis L of the prosthetic trunk 20. A take-off angle α of approximately 20-70 degrees, and preferably approximately 35-55 degrees or relatively close to 45 degrees, has been found to be advantageous because the prosthetic branch 40 can extend a relatively long overall distance, yet less directly in any one direction since it is approximately evenly split in X and Y planes. The alternative embodiment of FIGS. 3-4 is similar to FIGS. 1-2, however the embodiment of FIGS. 3-4 shows more of an axially straight branch take-off at an acute angle relative to the prosthetic trunk 20.

In either embodiment of FIGS. 1-2 or FIGS. 3-4, the prosthetic branch 40 may be attached to the prosthetic trunk 20 at any point along a length of the prosthetic trunk 20 extending between the first end 21 and the second end 23 of the prosthetic trunk 20. For example, the first end 41 of the prosthetic branch 40 may be attached to the prosthetic trunk 20 at an intermediate portion of the prosthetic trunk 20 as shown in FIGS. 1-4. Preferably, the prosthetic branch 40 may be attached to the prosthetic trunk 20 at a position that enables portions of the prosthetic trunk 20 proximal and distal of the prosthetic branch 40 to engage a wall of a body vessel and/or another prosthesis for treatment of an aneurysm.

The prosthetic branch 40 may be attached to the prosthetic trunk 20 by sutures, wire, staples, clips, bonding agents, or other methods that may be used to achieve a secure attachment. For example, the prosthetic branch 40 may be attached to the prosthetic trunk 20 by any method described in U.S. Patent Application Pub. No. 2006/0095118 by Hartley which is incorporated by reference herein in its entirety. Preferably, the graft body 45 of the prosthetic branch 40 may be attached to the graft body 25 of the prosthetic trunk 20 to form a fluid-tight seal. For example, the graft body 45 of the prosthetic branch 40 may be stitched to the graft body 25 of the prosthetic trunk 20.

An aperture 28 may be formed in the graft body 25 of the prosthetic trunk 20. The aperture 28 may be aligned with the first end opening 42 of the prosthetic branch 40 to enable fluid communication between the trunk lumen 29 and the branch lumen 49 through the aperture 28. In this manner, the prosthesis 10 may be configured to serve as a conduit for blood to flow through the trunk and branch lumens 29, 49 between the first end 21 of the prosthetic trunk 20 and the second ends 23, 43 of the prosthetic trunk 20 and the prosthetic branch 40, respectively.

The prosthesis 10 may be sized and shaped for placement within the vasculature of a patient for treatment of an aneurysmal body vessel. The preferred size and shape of the prosthesis 10 depend on the anatomy in which it is to be implanted. Physiological variables, deployment characteristics, and other factors also may contribute to the determination of a proper size and shape of the prosthesis 10. For example, the prosthesis 10 may have a size and shape suitable for placement at a common iliac bifurcation. To that end, the prosthetic trunk 20 may be configured for placement within a common iliac artery, and the prosthetic branch 40 may be configured to extend from the common iliac artery into an internal iliac artery. The prosthetic trunk 20 may have a diameter, for example, ranging from about 6 mm to about 36 mm. For example, in iliac artery applications, the diameter of the prosthetic trunk may range from about 6 mm to about 16 mm, but the diameter may be larger in other bodily passageways. The diameter of the prosthetic trunk 20 may be constant along the length of the prosthetic trunk. Alternatively, the prosthetic trunk 20 may be tapered such that the diameter of the prosthetic trunk 20 may vary along the length of the prosthetic trunk 20. The prosthetic branch 40 may have a diameter, for example, ranging from about 6 mm to about 24 mm. The diameter of the prosthetic branch 40 may be constant along the length of the prosthetic branch 40. Alternatively, the prosthetic branch 40 may be tapered such that the diameter of the prosthetic branch 40 may vary along the length of the prosthetic branch 40. The prosthesis 10 may be deployed in combination with various other prostheses to effectively bridge an aneurysmal portion of the vasculature.

It is further contemplated that a prosthesis may have multiple prosthetic branches extending from the prosthetic trunk 20. For example, the prosthesis may have two, three, or more prosthetic branches extending from the prosthetic trunk 20. The various branches may be attached to the prosthetic trunk 20 at varying longitudinal and/or circumferential positions with respect to the prosthetic trunk 20. In this manner, the prosthesis 10 may be configured for placement at various positions within the vasculature of the patient.

The graft bodies 25, 45 may be made of any material known in the art. For example, the graft bodies may be made of an expanded polytetrafluoroethylene (ePTFE), polytetrafluoroethylene, silicone, polyurethane, polyamide (nylon), as well as other flexible biocompatible materials. The graft bodies also can be made of known fabric graft materials such as woven polyester, polyetherurethanes, or polyethylene. The graft bodies also may include a bioremodelable material such as reconstituted or naturally-derived collagenous materials, extracellular matrix (ECM) material, submucosa, renal capsule membrane, dermal collagen, dura mater, pericardium, fascia lata, serosa, peritoneum or basement membrane layers, or intestinal submucosa, including small intestinal submucosa (SIS), stomach submucosa, urinary bladder submucosa, and uterine submucosa.

As shown in FIG. 4, the prosthetic trunk 20 further can include at least one support structure 60, such as a stent (it is noted that the support structure 60 of the prosthetic trunk 20 is omitted from FIGS. 1-3 and FIG. 6 for illustrative purposes of depicting and labeling features of the prosthetic branch 40). The support structure 60 may include a single, unitary structure or a plurality of independent structures. The support structure 60 and/or various portions thereof may be disposed on the inner surface and/or outer surface of the graft body 25. Multiple support structures 60 may be positioned at any points along a length of the prosthetic trunk 20, as generally depicted in FIG. 4.

The support structure 60 of the prosthetic trunk 20 may have any suitable stent pattern known in the art. One example of a stent pattern is the Z-stent or Gianturco stent design. Each Z-stent may include a series of substantially straight segments or struts interconnected by a series of bent segments or bends. The bent segments may include acute bends or apices. The Z-stents are arranged in a zigzag configuration in which the straight segments are set at angles relative to one another and are connected by the bent segments. The Z-stent design may be preferred for straight sections of the aorta. It provides both significant radial force as well as longitudinal support. In tortuous anatomy, branches, or fenestrations, it may be preferable to use alternative stents or modifications to the Z-stent design to avoid stent-to-stent contact. Alternative stents may include, for example, annular or helical stents. In some instances, it may be desirable to affix some of the stents to the internal surface of the prosthesis. The stents mentioned herein may be made from standard medical grade stainless steel. Other stents may be made from nitinol or other shape-memory materials.

In one embodiment, a plurality of support structures 60 are provided, where a first support structure 60*a* has a portion extending above the aperture 28 that leads into the prosthetic branch 40, and a second support structure 60*b* has a portion extending below the aperture 28, as depicted in FIG. 4. In this embodiment, the first and second support structures 60*a* and 60*b* may each comprise U-shaped regions that are positioned to accommodate the aperture 28 that leads into the prosthetic branch 40. Distal apices of the first support structure 60*a* may be aligned with proximal apices of the second support structure 60*b*, thereby allowing the respective U-shaped regions to form a generally elliptical shape surrounding the aperture 28. In this manner, the support structures 60 of the prosthetic trunk 20 extend around the prosthetic branch 40, i.e., do not overlap onto graft body 45 of the prosthetic branch 40.

Figure 5:
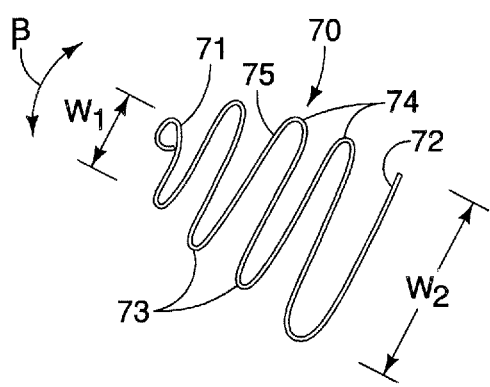
FIG. 5 is a front view of the support structure of FIGS. 1-4.

The prosthetic branch 40 comprises a support structure 70 having a proximal end 71 and a distal end 72, as best seen in FIG. 1 and FIG. 5. The support structure 70 is coupled to the graft body 45 of the prosthetic branch 40, at a location substantially overlapping (in a radially outward direction) the aperture 28 formed in the graft body 25 of the prosthetic trunk 20, as depicted in FIG. 1 and FIG. 3.

In one example, in an expanded state, the support structure 70 may be disposed in a manner such that its outer perimeter follows a shape of an outer perimeter 35 formed by the aperture 28 formed in the prosthetic trunk 20. In certain examples, the support structure 70 is positioned entirely within a radial boundary defined by the outer perimeter 35 of the aperture 28, as best seen in FIG. 3. In alternative embodiments, the support structure 70 may extend slightly beyond the outer perimeter 35 of the aperture 28, but preferably less than 10 percent of material of the support structure is disposed outside of a circumferential boundary formed by the outer perimeter 35. In this manner, the support structure 70 is substantially tailored to the shape of a particular outer perimeter of an aperture 28 in the prosthetic branch 20.

The proximal end 71 of the support structure 70 may comprise a width $w_1$, and the distal end 72 of the support structure 70 may comprise a width $w_2$, where the width $w_1$ is less than the width $w_2$, as shown in FIG. 5. In this manner, the relatively small width $w_1$ at the proximal end 71 of the support structure 70 may be better tailored to placement near a narrowed edge of the graft body 45 at the proximal end 41, as seen in FIG. 1. Conversely, the relatively large width $w_2$ at the distal end 72 of the support structure 70 conforms to a wider portion of the graft body 45, as the graft body 45 extends away from the opening 28.

The pattern of the support structure 70 may be formed in a manner similar to the formation of Z-stents, such as winding a single wire around a sequence of pins on a mandrel, in a manner and width generally corresponding to features at the proximal region of the prosthetic branch 40 to approximate its shape. The support structure 70 may comprise a shape-memory material, such as a nickel-titanium alloy, or another suitable material, which allows it to be inclined to assume a deployed state as depicted.

In the deployed state, the support stent 70 may comprise less than the 360 degree shape associated with conventional cylindrical stents. In particular, the support stent 70 is disposed less than 360 degrees around the perimeter of the branch portion 40.

The support stent 70 may comprise a generally flat profile in an expanded state, i.e., along strut segments 75 extending between opposing apices 73 and 74. Alternatively, the support structure 70 may comprise a concave curvature $\beta$ along the strut segments 75 formed between opposing apices 73 and 74, as depicted in FIG. 3 and FIG. 5. It should be noted that, in the present application, the term concave refers to a vantage point that generally begins inside of the main trunk lumen and looks radially outward towards the support stent 70 (in which case the support stent 70 would appear concave), as opposed to a convex curvature that would appear when the vantage point begins radially outside of the entire prosthesis and then looks radially inward towards the support stent 70.

In one example, the curvature $\beta$ along the strut segments 75 may be between about 10 and about 270 degrees, i.e., where 180 degrees forms a semi-circular shape. More preferably, the curvature $\beta$ may be between about 30 and about 240 degrees, which may correspond approximately to the circumferential distance that the aperture 28 spans along the outer perimeter of the prosthetic trunk 20, as depicted in FIG. 3.

Notably, the support structure 70 does not extend around both the prosthetic trunk 20 and the prosthetic branch 40. In this manner, the support structure 70 is more individually tailored to the shape of a proximal portion of the prosthetic branch 40 positioned radially outside of the aperture 28 in the prosthetic trunk 20. Accordingly, expansion support is provided to the prosthetic branch 40 radially outside of the aperture 28, to ensure that fluid flow and medical components can be easily delivered into the prosthetic branch 40 from the prosthetic trunk 20. Furthermore, the configuration or position of the prosthetic branch 40 is to not influenced by any structures that extend around both the prosthetic trunk 20 and the prosthetic branch 40.

In various embodiments, the prosthetic branch 40 may comprise one or more additional support structures that are disposed distally of the support structure 70. For example, a coil 90 may be disposed distally of the support structure 70, as shown in the embodiment of FIGS. 1-4. The coil 90 comprises proximal and distal ends 91 and 92, respectively, and is disposed in a 360 degree pattern around the graft body 45 of the prosthetic branch 40. Notably, the support structure 70 extends less than 360 degrees around a proximal region of the prosthetic branch 40, and then the coil 90 extends a full 360 degrees around a distal region of the prosthetic branch 40.

As depicted, the support structure 70 may be spaced apart from the coil 90. Each structure may be manufactured separately and then secured to the prosthetic branch 40. Optionally, the support structure 70 may be secured to the coil 90, e.g., with a connecting strut, solder, or other linking structure, thereby reducing structural gaps.

Alternatively, it is possible that the support structure 70 and the coil 90 could be manufactured using a single wire having the two distinct segments with different patterns, i.e., one less than 360 degrees where the support structure 70 is shown, and another helically spanning 360 degrees where the coil 90 is shown. In the event a single wire branch support structure is used for both the support structure 70 and the coil 90, it will be understood that the benefits obtained from the provision of the support structure 70, as explained above, will still be provided, simply at a proximal region of the single wire branch support structure.

Figure 6:
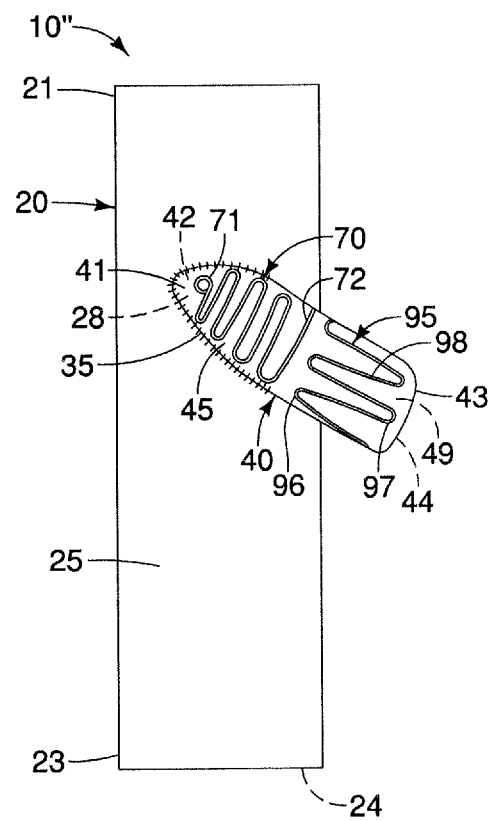
FIG. 6 is a front view of a further alternative prosthesis having a prosthetic branch comprising a support structure.

Referring to FIG. 6, in a further alternative embodiment, a second support structure in the form of a Z-stent 95 may be disposed distally of the support structure 70. The Z-stent 95 comprises proximal and distal ends 96 and 97, respectively, plus a plurality of expanding struts 98 therebetween, and is disposed in a 360 degree pattern around the graft body 45 of the prosthetic branch 40. It will be appreciated that alternative stent designs may be used instead of a Z-stent for support distal to the support structure 70.

The prosthesis 10 may be deployed, for example, in a common iliac artery such that the prosthetic branch 40 may be aligned with an internal iliac artery. The prosthesis 10 may be deployed using standard endoluminal techniques. For example, the prosthesis 10 may be deployed using the devices and/or methods described in U.S. Pat. No. 7,435,253 to Hartley et al. and U.S. Pat. No. 7,407,509 to Greenberg et al., which are incorporated by reference herein in their entirety.

In other examples, the prosthesis 10 may be deployed in an array of other vessels. For example, the prosthetic trunk 20 can be deployed in the descending aorta and the prosthetic branch 40 may extend into the renal arteries. It will be appreciated that the prosthesis 10 may be adapted for use in other vessels.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. An endoluminal prosthesis, comprising:
a prosthetic trunk comprising proximal and distal ends and a lumen extending therebetween;
a prosthetic branch comprising proximal and distal ends and a lumen extending therebetween, wherein the proximal end of the prosthetic branch is secured around an aperture formed in a side surface of the prosthetic trunk; and
a support structure coupled to the prosthetic branch, wherein a proximal end of the support structure comprises a first width, and a distal end of the support structure comprises a second width, wherein the first width is less than the second width,
wherein the support structure comprises undulations that are transverse to a longitudinal axis of the prosthetic branch and the amplitude of the undulations increases in a direction from the proximal end towards the distal end of the prosthetic branch.

2. The endoluminal prosthesis of claim 1, wherein the support structure extends less than 360 degrees circumferentially in a deployed state.

3. The endoluminal prosthesis of claim 2, wherein the support structure comprises a deployed state having a concave shape relative to the prosthetic trunk.

4. The endoluminal prosthesis of claim 1, wherein the support structure comprises boundaries forming a pattern that corresponds to a shape of the aperture in the prosthetic trunk.

5. The endoluminal prosthesis of claim 1, wherein the aperture formed in the prosthetic trunk comprises an outer perimeter, wherein in an expanded state the support structure is positioned above the aperture in a manner radially outside of the aperture and within axial boundaries formed by the outer perimeter of the aperture.

6. The endoluminal prosthesis of claim 1, wherein less than 10 percent of material of the support structure is disposed outside of a circumferential boundary formed by the outer perimeter of the aperture of the prosthetic trunk.

7. The endoluminal prosthesis of claim 1, further comprising a coil coupled to the prosthetic branch and disposed distally of the support structure.

8. The endoluminal prosthesis of claim 1, further comprising a Z-stent coupled to the prosthetic branch and disposed distally of the support structure.

9. The endoluminal prosthesis of claim 1, wherein the support structure lacks an attachment to the prosthetic trunk.

10. An endoluminal prosthesis, comprising:
a prosthetic trunk comprising proximal and distal ends and a lumen extending therebetween;
a prosthetic branch comprising proximal and distal ends and a lumen extending therebetween, wherein the proximal end of the prosthetic branch is secured around an aperture formed in a side surface of the prosthetic trunk; and
a support structure coupled to the prosthetic branch, wherein the support structure extends less than 360 degrees circumferentially in a deployed state,
wherein the support structure comprises undulations that are transverse to a longitudinal axis of the prosthetic branch and the amplitude of the undulations increases in a direction from the proximal end towards the distal end of the prosthetic branch.

11. The endoluminal prosthesis of claim 10, wherein a proximal end of the support structure comprises a first width, and a distal end of the support structure comprises a second width, wherein the first width is less than the second width.

12. The endoluminal prosthesis of claim 10, wherein the support structure comprises a deployed state having a concave shape relative to the prosthetic trunk.

13. The endoluminal prosthesis of claim 10, wherein the support structure comprises boundaries forming a pattern that corresponds to a shape of the aperture in the prosthetic trunk.

14. The endoluminal prosthesis of claim 10, wherein the aperture formed in the prosthetic trunk comprises an outer perimeter, wherein in an expanded state the support structure is positioned above the aperture in a manner radially outside of the aperture and within axial boundaries formed by the outer perimeter of the aperture.

15. The endoluminal prosthesis of claim 10, further comprising a coil coupled to the prosthetic branch and disposed distally of the support structure.

16. The endoluminal prosthesis of claim 10, further comprising a z-stent coupled to the prosthetic branch and disposed distally of the support structure.

17. The endoluminal prosthesis of claim 10, wherein the support structure lacks an attachment to the prosthetic trunk.

* * * * *